(12) United States Patent
Zhang et al.

(10) Patent No.: US 8,729,281 B2
(45) Date of Patent: May 20, 2014

(54) PRODUCTION OF HYDROXYMETHYLFURFURAL

(75) Inventors: Yugen Zhang, Singapore (SG); Jackie Y. Ying, Singapore (SG); Gen Yong, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 610 days.

(21) Appl. No.: 12/999,610

(22) PCT Filed: Jun. 18, 2008

(86) PCT No.: PCT/SG2008/000215
§ 371 (c)(1),
(2), (4) Date: Mar. 14, 2011

(87) PCT Pub. No.: WO2009/154566
PCT Pub. Date: Dec. 23, 2009

(65) Prior Publication Data
US 2012/0004430 A1   Jan. 5, 2012

(51) Int. Cl.
*C07D 307/02*   (2006.01)

(52) U.S. Cl.
USPC .......................................... 549/483; 549/506

(58) Field of Classification Search
USPC .................................. 549/506, 483
See application file for complete search history.

(56) References Cited

U.S. PATENT DOCUMENTS 5,728,839 A *  3/1998  Herrmann et al. ............ 548/103
7,758,897 B2 *  7/2010  Roettger et al. ............. 424/617
8,163,851 B2 *  4/2012  Ying et al. .................... 525/540

FOREIGN PATENT DOCUMENTS

WO   WO2006/063220   *  6/2006  ..................... 556/21
WO   WO 2008/019219 A1   2/2008

OTHER PUBLICATIONS

Kuster, Starch vol. 42 Nr. 8 pp. 314-321 (1990).*
Roman-Leshkov et al, Nature Letters vol. 447 pp. 982-985, (2007).*
McNaught, Alan D., "Nomenclature of carbohydrates (IUPAC Recommendations 1996)," Pure Appl. Chem., 1996, vol. 68, pp. 1919-2008.
Supplementary European Search Report, Sep. 30, 2011, EP Patent Application No. 08767294.5, 5 pages.
International Search Report from PCT/SG2008/000215 dated Sep. 17, 2008 (3 pages).
International Preliminary Report on Patentability from PCT/SG2008/000215 dated Jun. 18, 2010 (4 pages).
Hu et al.; "Conversion of fructose to 5-hydroxymethylfurfural using ionic liquids prepared from renewable materials"; 2008; *Green Chem.*; 10: 1280-1283.
Román-Leshkov et al.; "Phase modifiers promote efficient production of hydroxymethyl-furfural from fructose"; 2006; *Science*; 312: 1933-1937.
Yong et al.; "Efficient catalytic system for the selective production of 5-hydroxymethyl-furfural from glucose and fructose"; 2008; *Angew. Chem. Int. Ed.*; 47: 9345-9348.
Zhao et al.; "Metal chlorides in ionic liquid solvents convert sugars to 5-hydroxymethyl-furfural"; 2007; *Science*; 316: 1597-1600.

* cited by examiner

*Primary Examiner* — Andrew D Kosar
*Assistant Examiner* — Raymond Covington
(74) *Attorney, Agent, or Firm* — Kilpatrick Townsend & Stockton LLP

(57) ABSTRACT

The invention provides a process for making hydroxymethylfurfural comprising exposing a saccharide, e.g. glucose or fructose, to a metal complex of an N-heterocyclic carbene.

21 Claims, 3 Drawing Sheets

PRODUCTION OF HYDROXYMETHYLFURFURAL

CROSS-REFERENCE TO RELATED APPLICATION

The present application is the U.S. National Stage entry under §371 of International Application No. PCT/SG2008/000215, filed Jun. 18, 2008; the disclosure of which is herein incorporated by reference in its entirety for all purposes.

TECHNICAL FIELD

The present invention relates to a method of producing hydroxymethylfurfural.

BACKGROUND OF THE INVENTION

The diminishing fossil fuel reserves and the globe warming effects have become major concerns. The search for sustainable, alternative energy is of critical importance. Biofuels are highly attractive as the only sustainable source of liquid fuels currently. However, the replacement of petroleum feedstock by biomass is limited by the lack of highly efficient methods to selectively convert carbohydrates to chemical compounds for the biofuel production. A practical catalytic process that can transform the abundant biomass into versatile chemicals would also provide the chemical industry with renewable feedstocks.

Recently, much effort has been devoted towards converting biomass to 5-hydroxymethylfurfural (HMF), a versatile and key intermediate in biofuel chemistry and petroleum industry. HMF and its 2,5-disubstituted, furan derivatives can replace key petroleum-based building blocks. There are currently a number of catalysts that are active towards the dehydration of sugars to form HMF. However, most of them promote side-reactions that form undesired by-products and further rehydration of HMF to form levulinic acid and formic acid. They are also often limited to simple sugar feedstock, such as fructose.

Recent reports illustrate the use of 1-H-3-methyl imidazolium chloride (HMIM$^+$Cl$^-$) as a solvent and an acid catalyst to efficiently convert fructose to HMF with about 90% yield. However, such system has not be shown to convert glucose, which is a more stable and abundant sugar source. Dumesic's group has developed a two-phase system (aqueous/organic phases) for the separation and stabilization of HMF product ((a) Y. Roman-Leshkov, J. N. Chheda, J. A. Dumesic, *Science* 2006, 312, 1933; (b) J. N. Chheda, Y. Roman-Leshkov, J. A. Dumesic, *Green Chem.* 2007, 9, 342). Zhang's group has reported a metal chloride/ionic liquid system that gives moderate to good HMF yields for both fructose (83% with Pt or Rh chloride, 65% with CrCl$_2$) and glucose (a record high of 68% with CrCl$_2$) (H. Zhao, J. E. Holladay, H. Brown, Z. C. Zhang, *Science* 2007, 316, 1597).

There is a need for an improved method for converting both fructose and glucose to HMF in good to excellent yields, for example over about 80%. There is also a need for an improved method for converting other saccharides to HMF.

OBJECT OF THE INVENTION

It is an object of the present invention to substantially overcome or at least ameliorate one or more of the above disadvantages. It is a further object to at least partially satisfy at least one of the above needs.

SUMMARY OF THE INVENTION

In a first aspect of the invention there is provided a process for making hydroxymethylfurfural comprising exposing a saccharide to a metal complex of an N-heterocyclic carbene.

The following options may be used in conjunction with the first aspect, either individually or in any suitable combination.

The saccharide may comprise a monosaccharide. It may comprise a disaccharide. It may comprise an oligosaccharide. It may comprise a polysaccharide. It may comprise (or may be) a mixture of any two or more of these. The monosaccharide may comprise fructose, glucose or a mixture of these. The disaccharide may be sucrose.

The exposing may be conducted in a dipolar aprotic solvent. The solvent may be, or may comprise, an ionic liquid. The ionic liquid may be, or may comprise, an imidazolium salt (e.g. halide, for example chloride). It may be, or may comprise, 1-butyl-3-methylimidazolium chloride.

The metal complex may be a transition metal complex. It may be a chromium complex or a titanium complex or a tungsten complex or a molybdenum complex or a nickel complex or a palladium complex or a ruthenium complex or an aluminium complex, or it may be a mixture of any two or more of these. It may be a CrII complex or a CrIII complex.

The N-heterocyclic carbene may be monomeric. It may be dimeric. It may be oligomeric. It may be polymeric. The metal complex of the N-heterocyclic carbene may be a metal complex of an N-imidazole carbene for example a metal complex of a monomeric N-imidazole carbene or of a polymeric N-imidazole carbene.

The process may also comprise the step of generating the metal complex of the N-heterocyclic carbene. The step of generating the metal complex of the N-heterocyclic carbene may comprise reacting a nitrogen heterocycle salt with a base in the presence of a salt of the metal. The base may be potassium t-butoxide.

The process may additionally comprise isolating the hydroxymethyl furfural.

The monosaccharide may be fructose and the yield of hydroxymethyl furfural may be greater than about 80%. The monosaccharide may be glucose and the yield of hydroxymethyl furfural may be greater than about 70%.

The metal complex of an N-heterocyclic carbene may be recycled following removal of the hydroxymethylfurfural from the reaction mixture. In the event that the exposing is conducted in an ionic liquid, said ionic liquid may be recycled following removal of the hydroxymethylfurfural from the reaction mixture. The recycling may comprise heating the reaction mixture following removal of the hydroxymethylfurfural therefrom for sufficient time to remove volatile substances therefrom.

In one embodiment there is provided a process for making hydroxymethylfurfural comprising exposing fructose, glucose or a mixture of these to a chromium complex of an N-heterocyclic carbene in an ionic liquid.

In another embodiment there is provided a process for making hydroxymethylfurfural comprising:
  generating a chromium complex of an N-heterocyclic carbene; and
  exposing fructose, glucose or a mixture of these to the chromium complex of the N-heterocyclic carbene in an ionic liquid.

In another embodiment there is provided a process for making hydroxymethylfurfural comprising:
  reacting a nitrogen heterocycle with a base in the presence of a chromium salt so as to generate a chromium complex of an N-heterocyclic carbene; and exposing fructose, glucose or a mixture of these to the chromium complex of the N-heterocyclic carbene in an ionic liquid.

The invention also provides hydroxymethyl furfural when made by the process of the first aspect.

In a second aspect of the invention there is provided use of a metal complex of an N-heterocyclic carbene for making hydroxymethyl furfural.

In a third aspect of the invention there is provided use of hydroxymethylfurfural made by the process of the first aspect for producing a fuel, e.g. a biofuel.

In a fourth aspect of the invention there is provided a biofuel made using hydroxymethylfurfural which has been made by the process of the first aspect.

BRIEF DESCRIPTION OF THE DRAWINGS

A preferred embodiment of the present invention will now be described, by way of an example only, with reference to the accompanying drawings wherein.

DETAILED DESCRIPTION OF THE PREFERRED EMBODIMENTS

Figure 1:
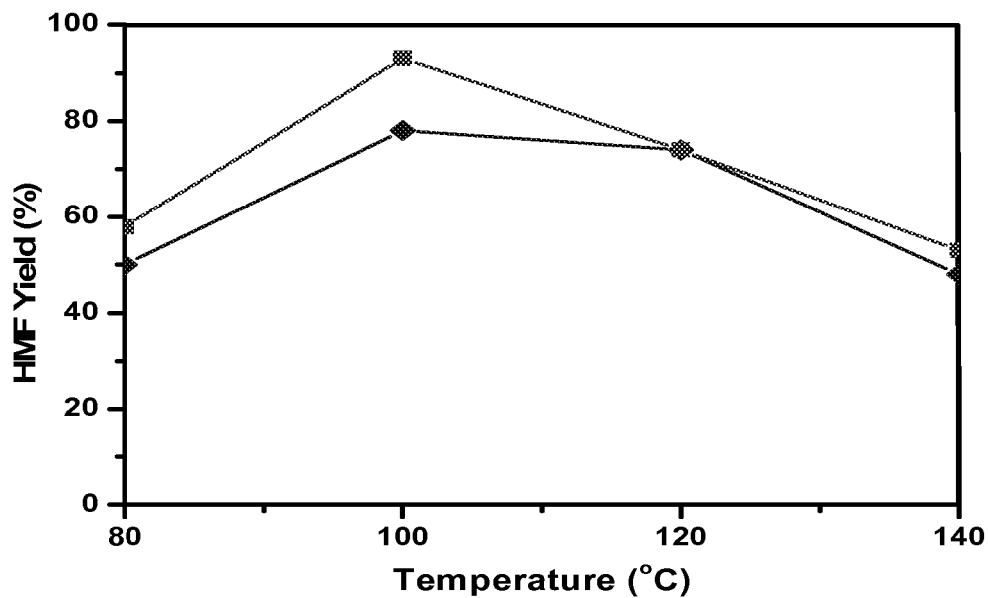
FIG. 1 is a graph showing the effect of reaction temperature on HMF yield from (■) fructose and (♦) glucose over 9 mol % of 6-$CrCl_2$ (substrate/BMIM weight ratio=0.2, 6 h)

The inventors have found that N-heterocyclic carbene-metal complexes are capable of catalysing the conversion of saccharides such as glucose or fructose to hydroxymethylfurfural (5-(hydroxymethyl)-2-furaldehyde; HMF). The reaction proceeds in relatively high yield, particularly when an ionic liquid solvent is employed. Mixtures of suitable saccharides may also be used. The reaction may be used with monosaccharides (e.g. glucose, fructose), disaccharides (e.g. sucrose), oligosaccharides or polysaccharides (e.g. starch, cellulose). The saccharide may be a hexose or a mixture of hexoses, or a dimer, oligomer or polymer or copolymer of a hexose or of a mixture thereof. The reaction described herein has the advantage that it uses relatively inexpensive and/or readily available substrates, which, in some cases, represent waste materials. For example, 30% HMF yield was achieved by conversion of cellulose according to the process of the invention. Polymeric NHC based catalysts were found to provide slightly lower HMF yields from fructose and glucose than their monomeric counterparts, however the polymeric NHC based catalysts have the advantage of better recyclability than the monomeric counterparts. The N-heterocyclic carbene-metal complex may be used in conjunction with an acid catalyst. The acid catalyst may be a heterogeneous acid catalyst. It may be a solid heterogeneous acid catalyst. It may for example be a zeolyte. This may be particularly beneficial in cases where the saccharide is a disaccharide, oligosaccharide or polysaccharide. The process may comprise hydrolysis of the disaccharide, oligosaccharide or polysaccharide. The hydrolysis may be an in situ hydrolysis. It may be catalysed by the acid catalyst.

Suitable solvents for the process are dipolar aprotic solvents. The solvent may comprise, or may be, an ionic liquid. A suitable ionic liquid is 1-butyl-3-methylimidazolium chloride. Other imidazolium salts are also suitable. The counterion of the imidazolium salt may be a halide, for example chloride. The solvent may be a mixture of solvents, for example a mixture of dipolar aprotic solvents. The solvent may comprise an ionic liquid together with a different dipolar aprotic solvent (such as dimethylformamide, dimethylsulfoxide, hexamethylphosphoramide etc.) The solvent may primarily consist of the ionic liquid, e.g. greater than about 50%, or greater than about 60, 70, 80 or 90% by weight or volume.

The metal complex of the N-heterocyclic carbene may be a metal complex of an N-imidazole carbene. It may be a chromium II or chromium III complex of an N-heterocyclic carbene. The N-heterocyclic carbene (NHC) may be derived from imidazolium salt, or from a substituted imidazolium salt, in particular an N,N'-disubstituted imidazolium salt. The imidazolium salt may be a bisimidazolium salt, e.g. a pyridine bisimidazolium salt. The NHC may be derived from an imidazolinium salt, or from a substituted imidazolinium salt in particular an N,N'-disubstituted imidazolinium salt. The imidazolinium salt may be a imidazolinium salt, e.g. a pyridine imidazolinium salt. The NHC may be an $\alpha,\alpha'$-dinitrogen carbon. Each of the $\alpha$-nitrogen atoms may be substituted. They may each, independently, be substituted with a bulky group. They may both substituted with a bulky group (optionally with the same bulky group). Suitable bulky groups are t-butyl, neopentyl, 2,6-dimethylphenyl, 2,4,6-trimethylphenyl, 2,6-diisopropylphenyl, 2,4,6-triisopropylphenyl etc. The substituents on the nitrogen atoms may be, independently, alkyl groups or aryl groups or heteroaryl groups. Thus the NHC may be an imidazol-2-ylidene. It may be an N,N'-disubstituted imidazol-2-ylidine, i.e. a 1,3-disubstituted imidazol-2-ylidine. It may be an imidazolin-2-ylidine. It may be an N,N'-disubstituted imidazolin-2-ylidine, i.e. a 1,3-disubstituted imidazolin-2-ylidine.

The metal complex of the N-heterocyclic carbene may be soluble in the solvent (or in the reaction mixture) or it may be insoluble therein. It may be used as a homogeneous catalyst or as a heterogeneous catalyst. Particularly in the case of a polymeric complex, it may be used as a heterogeneous catalyst. If the complex is used as a heterogeneous catalyst, it may, optionally, subsequently be removed from the reaction mixture by precipitation, filtration, centrifugation or some combination of these. It may then be reused in a subsequent reaction if desired. It may be reused with a loss of catalytic activity of less than about 10%, or less than about 5, 2 or 1%.

The metal complex of the N-heterocyclic carbene may be generated from the corresponding nitrogen heterocycle salt by reaction with a base in the presence of a salt of the metal. The base may be potassium t-butoxide or some other strong base, for example sodium hydride, potassium hydride, NaN(TMS)$_2$ etc. The base may be a sufficiently strong base to be capable of converting the nitrogen heterocycle salt to the corresponding N-heterocyclic carbene. Thus for example to generate a metal complex of a 1,3-disubstituted imidazol-2-ylidine, the corresponding 1,3-disubstituted imidazolium salt may be treated with a strong base in the presence of a salt of the metal. The nitrogen heterocycle salt may be a halide, e.g. chloride, bromide or iodide, or may have some other counterion. The salt of the metal may be a halide, e.g. chloride, bromide or iodide, or may have some other counterion. The counterion of the salt of the metal may be the same as or different to the counterion of the nitrogen heterocycle salt. The metal may be a transition metal. The metal may be chromium, titanium, tungsten, molybdenum, nickel, palladium, ruthenium or aluminium, or may be a mixture of any two or more of these. The reaction may be conducted in a solvent. The solvent may be a dipolar aprotic solvent. It may be a solvent that is not base sensitive. It may be for example DMF, DMSO, HMPT, HMPA or some other suitable solvent. It may be a solvent for the heterocycle salt. It may be a' solvent for the base. It may be a solvent for the metal salt. It may be a solvent for the metal complex of the NHC. It may be desirable to heat the reaction mixture in order to form the metal complex of the NHC. In some cases heating may not be used. Suitable temperatures are between about 20 and about 100° C., or about 30 to 100, 50 to 100, 20 to 80, 20 to 50, 30 to 70, 50 to 80, 70 to 100 or 70 to 90° C., e.g. about 20, 30, 40, 50, 60, 70, 80, 90 or 100° C. The reaction may be conducted for sufficient time for substantially complete conversion. It may be conducted for about 1 to about 6 hours, or about 1 to 3, 3 to 6 or 2 to 5 hours, e.g. about 1, 2, 3, 4, 5 or 6 hours. The temperature and time should be sufficient to form the metal complex of the NHC.

In the process of the invention, the sugar (fructose and/or sucrose) may be mixed with the solvent (e.g. ionic liquid). A suitable ratio of sugar to solvent is about 20% w/w, or about 5 to about 30%, or about 5 to 25, 5 to 20, 5 to 10, 10 to 30, 20 to 30, 10 to 25 or 15 to 25%, e.g. about 5, 10, 15, 20, 25 or 30%. In the case of glucose as substrate, this may be as high as 50, 60, 70, 80, 90 or even 100% (e.g. may also be about 40, 50, 60, 70, 80, 90 or 100% w/w). The catalyst (metal-carbene complex) may then be added. A suitable addition ratio may be about 1 to about 15 mol % relative to the sugar, or about 1 to 10, 1 to 5, 5 to 15, 10 to 15, 5 to 10, 1 to 3, 2 to 5 or 2 to 4%, e.g. about 1, 2, 3, 4, 5, 6, 7, 8, 9, 10, 11, 12, 13, 14 or 15 mol %. The addition ratio should be sufficient to obtain an acceptable, optionally an optimal, yield of product. The reaction may be conducted at a temperature of about 80 to about 120° C., or about 80 to 100, 80 to 90, 90 to 120, 100 to 120 or 90 to 100° C., e.g. about 870, 85, 90, 95, 100, 105, 110, 115 or 120° C., or at some other suitable temperature. The temperature may be selected so as to provide an optimum yield or to obtain an acceptable yield. It may be selected to provide a trade-off between poor yield and excessive by-product formation. It may be selected to provide an acceptably low yield of by-product. The reaction may be conducted for between about 2 and about 10 hours, or about 2 to 8, 2 to 6, 4 to 10, 6 to 10, 4 to 8 or 5 to 7 hours, or about 2, 3, 4, 5, 6, 7, 8, 9 or 10 hours. The time may depend on the temperature. The reaction may be conducted under an inert atmosphere, e.g. nitrogen, carbon dioxide, helium, neon, argon or a mixture of any two or more of these, or it may be conducted in air or some other oxygen containing gas mixture. In some cases it may be conducted under reduced pressure, e.g. an absolute pressure of about 0.2 atmospheres or less, or about 0.1, 0.05, 0.02 or 0.01 atmospheres or less. In such cases at least some byproducts may be removed as they are formed. This may enable recycling of the metal complex of the N-heterocyclic, carbene and/or of the solvent without a separate step of removing the volatiles.

The hydroxymethylfurfural product may be isolated from the reaction mixture by known methods. These include solvent extraction (e.g. diethyl ether extraction), water washing, column chromatography, gas chromatography, hplc or a combination of any two or more of these.

The reaction may be conducted using fructose as a substrate, or glucose, or with a mixture of the two. If suitable conditions are used (as described above), a yield of hydroxymethyl furfural may be at least about 70%, at least about 75, 80, 85 or 90%. Commonly the yield from glucose and from glucose will be different.

The metal complex of an N-heterocyclic carbene may be recycled following removal of the hydroxymethylfurfural from the reaction mixture. In particular, it may be reused in a subsequent reaction, said subsequent reaction being the process for making hydroxymethylfurfural described herein. This provides cost savings in the process and can be achieved with little or no loss of yield of hydroxymethyl furfural (e.g. less than about 5%, loss of yield, or less than about 4, 3 or 2% loss of yield). In the event that the exposing is conducted in an ionic liquid, the ionic liquid may also be recycled. Commonly, the product hydroxymethylfurfural is removed from the reaction mixture by solvent extraction (optionally repeated solvent extraction). The reaction mixture (with the hydroxymethyl furfural removed) may then be treated so as to remove volatile materials (e.g. substantially all volatile materials, or at least about 80, 85, 90, 95 or 98% of volatile materials) by heating and/or applying a vacuum thereto. Alternatively or additionally, removal of volatiles may be conducted prior to removal of the hydroxymethylfurfural. In this context, "volatile" materials are considered to have a boiling point of about 100° C. or less. The heating may be at a temperature of about 80 to about 150° C., or about 80 to 120, 80 to 100, 100 to 150, 120 to 150, 100 to 120 or 90 to 110° C., e.g. about 80, 90, 100, 110, 120, 130, 140 or 150° C. The vacuum may have an absolute pressure of about 0.2 atmospheres or less, or about 0.1, 0.05, 0.02 or 0.01 atmospheres or less. The time for said treating may be sufficient under the treatment conditions to remove the desired proportions of volatile materials. It may be about 1 to about 5 hours, or about 1 to 3, 2 to 5 or 1.5 to 2.5 hours, e.g. about 1, 1.5, 2, 2.5, 3, 3.5, 4, 4.5 or 5 hours. The heating/vacuum may be applied in a suitable apparatus, e.g. a vacuum chamber, a cyclone evaporator or some other suitable apparatus. In some cases no vacuum is applied.

The production of hydroxymethylfurfural according to the present invention may be conducted as a continuous process. In an example, saccharide(s) and catalyst are continuously added to an addition zone of a reaction cycle, the resulting mixture is then held at a suitable temperature for a suitable time (as described earlier) for reaction to form hydroxymethylfurfural in a reaction zone of the reaction cycle, volatiles and hydroxymethylfurfural are continuously separated in a separation zone and the solvent and catalyst recycled to the addition zone for reuse. The reaction zone may have vacuum applied to it, so that volatiles are removed during the reaction, and hydroxymethylfurfural is removed subsequently in the separation zone.

Thus in many embodiments the present invention presents a new Cr—N-heterocyclic carbene (NHC)/ionic liquid system that selectively produces hydroxylmethylfurfural (HMF) from glucose and fructose. This novel catalyst achieved the highest efficiency known from both fructose and glucose feedstocks. The HMF yields were as high as 96% and 82% from fructose and glucose respectively. The new system provided high selectivity towards HMF, and tolerance towards high substrate loading. It also allowed for ease of recycling of catalyst and ionic liquid.

The inventors have investigated N-heterocyclic carbene (NHC)-metal complexes as catalysts for the sugar dehydration reaction. These ligands offered a great deal of flexibility towards modifying the catalytic activity by varying the stereo and electronic properties of NHCs. The conversions of fructose and glucose were tested over 1-butyl-3-methylimidazolium chloride (BMIM) with different catalysts (Scheme 1). The NHC-metal complexes were pre-generated by mixing imidazolium salts, KO$^t$Bu and metal chlorides in N,N-dimethylformamide (DMF) under heating for several hours before adding to the reaction system. In a typical reaction protocol, 100 mg of sugar was mixed with 500 mg of BMIM and 2 mol % pre-prepared Cr-NHC catalyst. The reaction mixture was kept at 100° C. for 6 h. HMF was extracted by ether (three times). All experiments were repeated, and the HMF yield was confirmed by both GC and NMR of the isolated product.

Scheme 1. Conversion of sugars to HMF over NHC-metal catalysts.

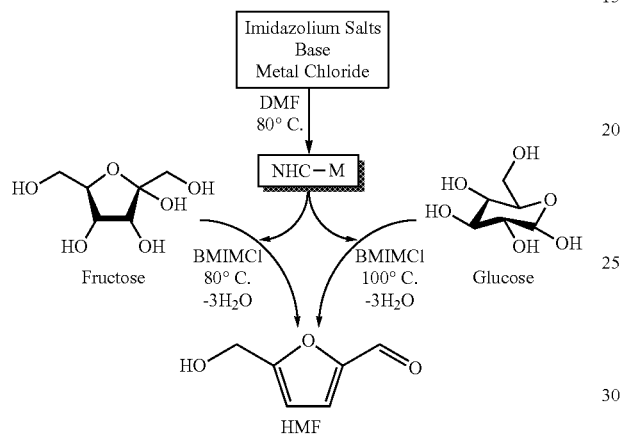

Several metals were selected for the screening studies, but only Cr(II) and Cr(III) gave promising results. Unlike the previously reported metal chloride/ionic liquid system, herein Cr(II) and Cr(III) showed similar activities toward converting fructose or glucose to HMF (Table 1).

TABLE 1

Conversion of sugars to HMF by NHC—Cr catalysts.[a]

| entry | catalyst | Yield from fructose (%)[b] | | Yield from glucose (%)[b] | |
|---|---|---|---|---|---|
| | | BMIM | DMSO | BMIM | DMSO |
| 1 | 1-CrCl$_2$ | 65 | 28 | 66 | 25 |
| 2 | 2-CrCl$_2$ | 68 | 32 | 65 | 25 |
| 3 | 3-CrCl$_2$ | 76 | 39 | 62 | 26 |
| 4 | 4-CrCl$_2$ | 89 | 52 | 90 | 31 |
| 5 | 5-CrCl$_2$ | 76 | — | 50 | — |
| 6 | 6-CrCl$_2$ | 96 | 41 | 81 | 32 |
| 7 | 7-CrCl$_2$ | 93 | — | 70 | 26 |
| 8 | 8-(CrCl$_2$)$_2$ | — | — | 81 | — |
| 9 | 8-CrCl$_2$ | 74 | — | 14 | — |
| 10 | 4-CrCl$_3$ | 90 | 40 | 78 | 30 |
| 11 | 5-CrCl$_3$ | 77 | — | 72 | — |
| 12 | 6-CrCl$_3$ | 96 | 40 | 78 | 32 |
| 13 | 7-CrCl$_3$ | 83 | — | 81 | — |
| 14[c] | 6-CrCl$_3$ | 82 | — | 65 | — |
| 15[d] | 6-CrCl$_3$ | — | — | 76 | — |
| 16[e] | 6-CrCl$_3$ | 96 | — | 76 | — |
| 17[f] | 6-CrCl$_3$ | 98 | — | 76 | — |

[a]Reaction conditions: 500 mg of solvent, 50 mg of sugar, 9 mol % of catalyst, 100° C., 6 h, in air, unless otherwise stated.
[b]Yield was determined by gas chromatography (GC) with internal standard and isolated pure product.
[c]Reaction was conducted under argon.
[d]9 mol % of bipyridine was added to the reaction system.
[e]Recycled reaction system from entry 12.
[f]Recycled reaction system from entry 16.

Structures of carbenes used in the reactions summarized in Table 1 are shown below.

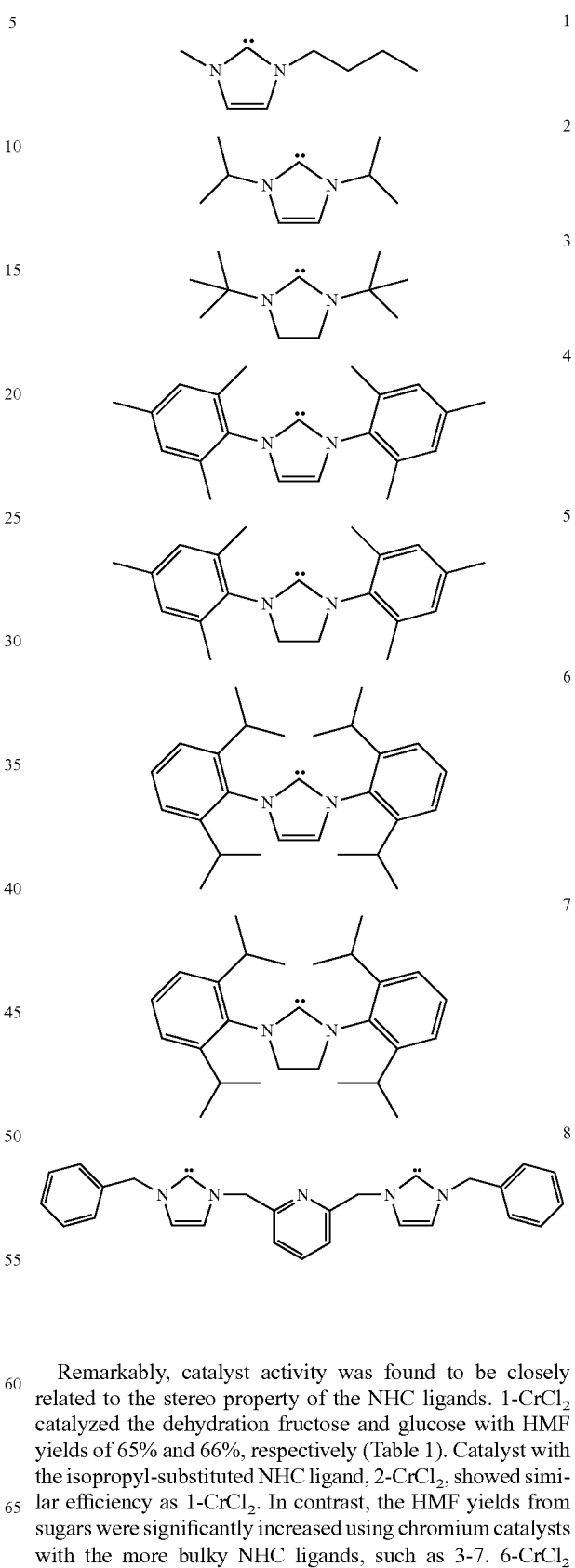

Remarkably, catalyst activity was found to be closely related to the stereo property of the NHC ligands. 1-CrCl$_2$ catalyzed the dehydration fructose and glucose with HMF yields of 65% and 66%, respectively (Table 1). Catalyst with the isopropyl-substituted NHC ligand, 2-CrCl$_2$, showed similar efficiency as 1-CrCl$_2$. In contrast, the HMF yields from sugars were significantly increased using chromium catalysts with the more bulky NHC ligands, such as 3-7. 6-CrCl$_2$ system provided a HMF yield as high as 96% from fructose. It also gave a HMF yield of 81% from glucose, which was a record high efficiency for glucose feedstock. There was no difference in yield for the metal catalysts with saturated vs. unsaturated NHC ligands. The catalysts with the most bulky NHC ligand, 1,3-bis(2,6-diisopropylphenyl)imidazolylidene 6 and 1,3-bis(2,6-diisopropyl)phenylimidazolinylidene 7 provided the highest yields. To better understand the details of this reaction, bidentate ligand 8 was examined. Interestingly, catalyst 8-(Cr)$_2$ gave a good HMF yield (81%) from glucose, while 8-(Cr)$_1$ showed a poor HMF yield (14%). These results suggested that an over-crowded complex would have a lower activity in binding with substrates and initiating the reaction. Control reaction without catalyst showed a very low HMF yield (less than 40% and 1% from fructose and glucose, respectively). The reaction temperature was investigated between 80° C. and 100° C. for both fructose and glucose. Lower temperature led to a lower HMF yield: higher temperature gave rise to byproducts, mainly diformylfuran (DFF) (see FIG. 1).

Figure 2:
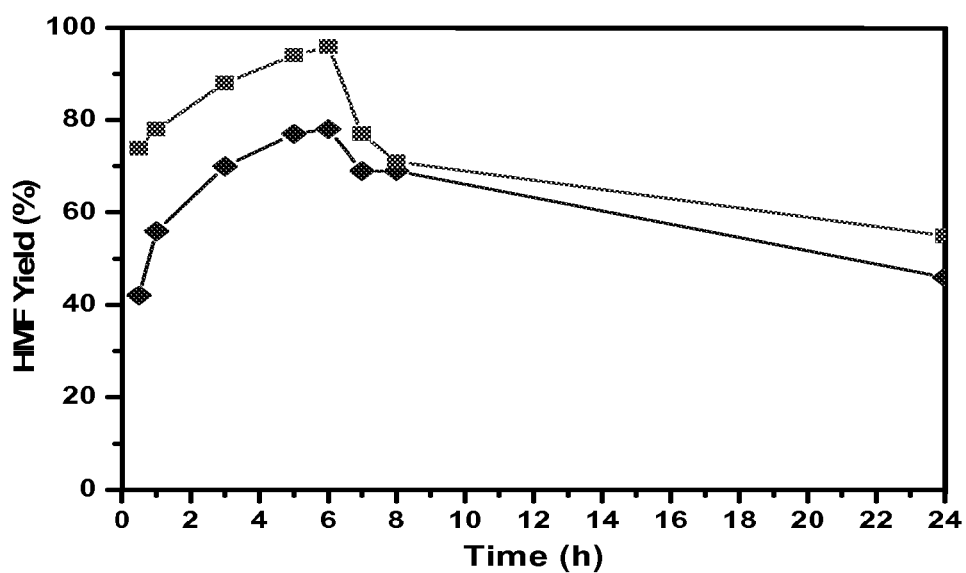
FIG. 2 is a graph showing the effect of reaction time on HMF yield from (■) fructose and (♦) glucose over 9 mol % of 6-$CrCl_2$ (substrate/BMIM weight ratio=0.2, 100° C.)
Figure 3:
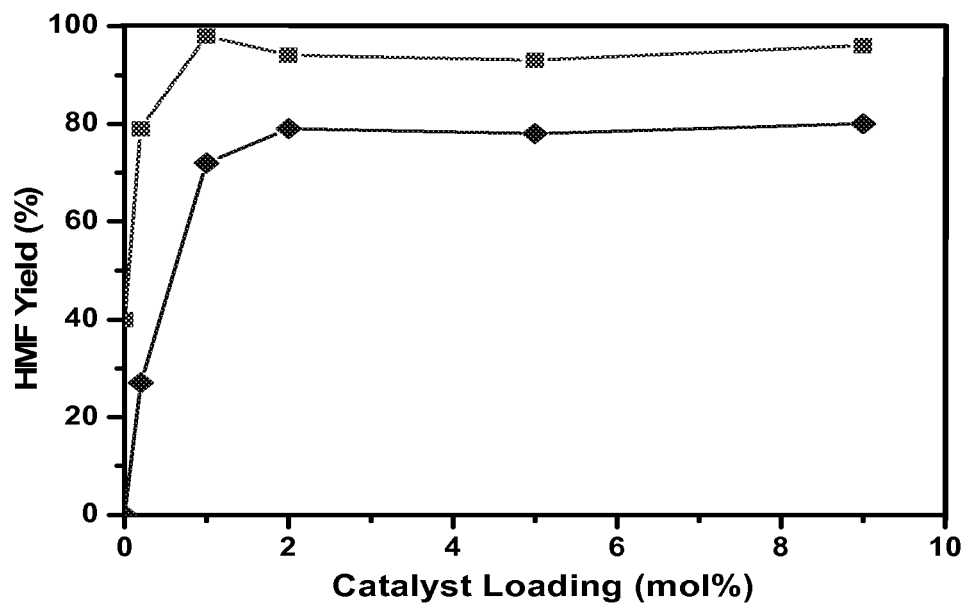
FIG. 3 is a graph showing the effect of 6-$CrCl_2$ loading on HMF yield from (■) fructose and (♦) glucose (substrate/BMIM weight ratio=0.2, 6 h, 100° C.)

Kinetics studies of this reaction over 6-CrCl$_2$ showed that the HMF yield peaked at our standard reaction condition of 6 h for both fructose and glucose (see FIG. 2). The HMF yield gradually decreased at reaction periods beyond 6 h. This could be due to the slow decomposition of HMF in the reaction system. HMF yield for fructose and glucose after 6 h began to decrease as the NHC-Cr catalyst loading was reduced to less than 1 mol % (see FIG. 3). Generally, lower catalyst loading would require a longer reaction time to achieve a high conversion. However, in this system, the product could decompose under the reaction condition, so longer reaction time would lead to lower yield of the desired product. Thus, if a low catalyst loading of 1 mol % is to be employed, other reaction conditions have to be optimized to maximize the HMF yield.

Figure 4:
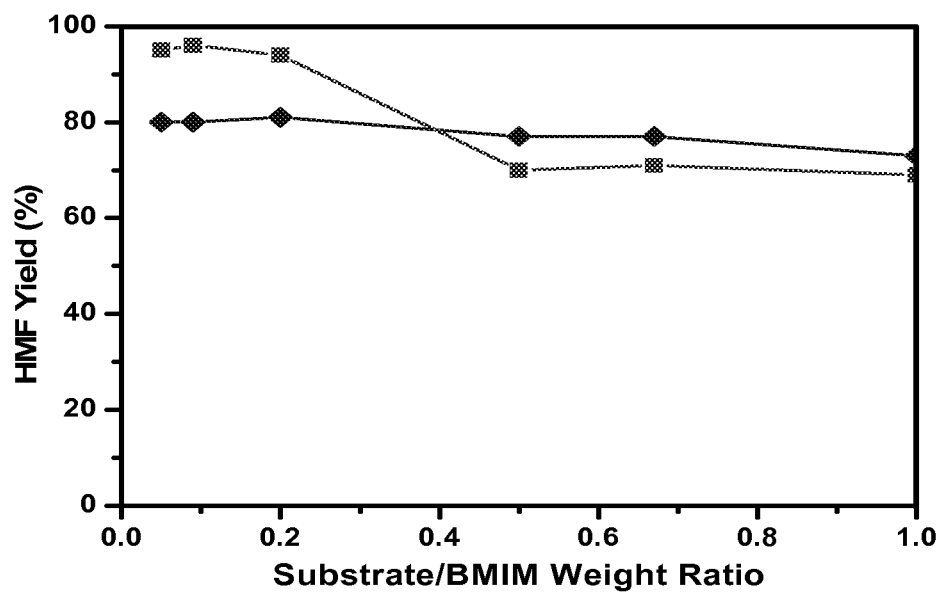
FIG. 4 is a graph showing the effect of substrate loading on HMF yield from (■) fructose and (♦) glucose over 9 mol % of 6-$CrCl_2$ (6 h, 100° C.)

The substrate/solvent weight ratio was also found to be important for the overall efficiency of the reaction system (see FIG. 4). When the fructose/BMIM weight ratio was increased from 0.05 to 0.2, the HMF yield changed slightly from 95% to 94%. As the fructose/ionic liquid weight ratio increased from 0.2 to 0.5, the HMF yield decreased substantially to 70%. Further increase in the fructose/ionic liquid weight ratio did not lead to significant variation in HMF yield. Remarkably, the HMF yields remained rather unaffected (81-77%) as the glucose/BMIM weight ratio was varied from 0.05 to 0.67. The HMF yield was only slightly decreased (to 73%) when the glucose/BMIM weight ratio was increased to 1.0. In this case, BMIM acted more like an assisting reagent than a solvent.

The different behavior of fructose and glucose in FIG. 4 suggested different possible reaction mechanisms for the two feedstocks. In the latter, glucose might be first converted to fructose and subsequently to HMF over the NHC-Cr catalyst (see Scheme 2). In this case, fructose concentration would be relatively low even when the glucose substrate loading was high since fructose was merely an intermediate in the conversion of glucose to HMF. Interestingly, HMF yields of about 15% lower were obtained for the reaction conducted in argon vs. in air (Table 1, entry 14 vs. entry 12). The NHC-Cr catalysts were also tested in dimethylsulfoxide (DMSO). Much lower HMF yields were obtained from fructose (28-52%) and glucose (25-32%) in this solvent (see Table 1). Again, catalysts with bulky NHC ligands showed higher efficiency in the DMSO system.

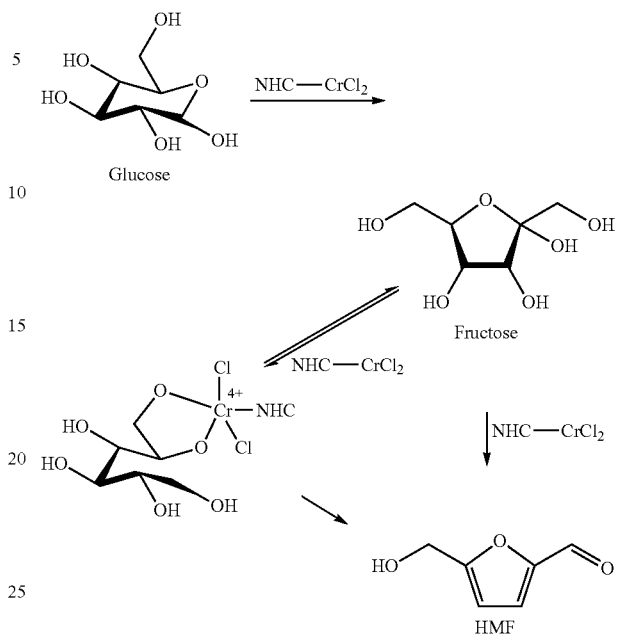

Scheme 2. Proposed schematic for the conversion of glucose to HMF

The high efficiency of the catalyst and the high substrate loading render the process of the invention very attractive for industrial scale-up. This reaction process would also allow for the continuous extraction of product, and the recycling of catalyst NHC-Cr and ionic liquid. HMF would be the sole product in ether extraction when the conversion of glucose and fructose was conducted at temperatures below 100° C. After the ether extraction, the reaction medium was preheated at 100° C. for 2 h to remove the low boiling point components, such as ether and water, and then directly used in the next run by adding the sugar substrate. The recycled reaction system retained high activity in the conversion of glucose and fructose to HMF (Table 1, entries 16 and 17). The high substrate loading and the ease of catalyst and ionic liquid recycling make this system attractive for industrial applications.

Figure 5:
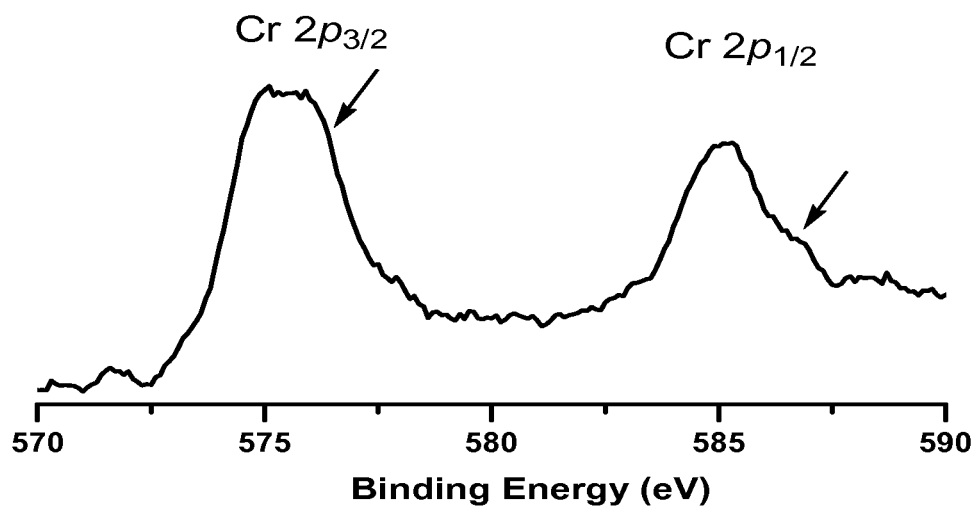
FIG. 5 is an XPS spectrum of the reaction intermediate of 6-$CrCl_2$.

The present results clearly suggested that NHC-CrCl$_x$ complexes play a key role in glucose dehydration in BMIM. Bulky NHC ligand prevented chromium from forming multiple NHC coordination in BMIM, reducing the catalytic activity as in the case of 8-(Cr)$_1$. In contrast, no inhibition effect was observed with the addition of bipyridine ligand in the case of 6-CrCl$_3$ (HMF yield of 76% from glucose) (Table 1, entry 15). Glucose is proposed to be converted to fructose or HMF by NHC-Cr complex via redox processes (see Scheme 2). This may explain why chromium, which has versatile oxidation states, is suitable for this reaction. X-ray photoelectron spectroscopy (XPS) indicated split peaks for Cr 2p$_{3/2}$ and 2p$_{1/2}$ peaks for the reaction intermediate of 6-CrCl$_2$. The shoulder of Cr 2p$_{3/2}$ and Cr 2p$_{1/2}$ peaks at 577 eV and 587 eV, respectively, indicated the presence of oxidized Cr species (see FIG. 5).

In summary, a new NHC-Cr/ionic liquid system has been developed for the selective conversion of sugars to HMF. This new system achieved excellent efficiency and the highest HMF yields reported thus far for both fructose and glucose feedstocks. The HMF yields were as high as 96% and 82% for fructose and glucose, respectively. The new system also allowed for ease of catalyst and ionic liquid recycling, provided sole HMF product by simple extraction, and was tolerant towards high substrate loading.

The invention claimed is:

1. A process for making hydroxymethylfurfural comprising reacting a saccharide with a metal complex of an N-heterocyclic carbene, wherein said saccharide is a hexose or a mixture of hexoses, or a dimer, oligomer or polymer or copolymer of a hexose or of a mixture thereof.

2. The process of claim 1 wherein the saccharide comprises a monosaccharide.

3. The process of claim 2 wherein the monosaccharide comprises fructose, glucose or a mixture of these.

4. The process of claim 1 wherein the is conducted in a dipolar aprotic solvent.

5. The process of claim 4 wherein the solvent is an ionic liquid.

6. The process of claim 5 wherein the ionic liquid is 1-butyl-3-methylimidazolium chloride.

7. The process of claim 1 wherein the N-heterocyclic carbene is a monomeric N-heterocyclic carbene.

8. The process of claim 1 wherein the N-heterocyclic carbene is a polymeric N-heterocyclic carbene.

9. The process of claim 1 wherein the metal complex is a transition metal complex.

10. The process of claim 9 wherein the transition metal complex is a chromium complex.

11. The process of claim 1 wherein the metal complex of the N-heterocyclic carbene is a metal complex of an N-imidazole carbene.

12. The process of claim 1 comprising the step of generating the metal complex of the N-heterocyclic carbene.

13. The process of claim 12 wherein the step of generating the metal complex of the N-heterocyclic carbene comprises reacting a nitrogen heterocycle salt with a base in the presence of a salt of the metal.

14. The process of claim 13 wherein the base is potassium t-butoxide.

15. The process of claim 1 additionally comprising isolating the hydroxymethylfurfural.

16. The process of claim 1 wherein the saccharide is fructose and the yield of hydroxymethylfurfural is greater than about 80%.

17. The process of claim 1 wherein the saccharide is glucose and the yield of hydroxymethylfurfural is greater than about 70%.

18. The process of claim 1 wherein the metal complex of the N-heterocyclic carbene is recycled following removal of the hydroxymethylfurfural from the reaction mixture.

19. The process claim 1 wherein the reacting is conducted in an ionic liquid, and said ionic liquid is recycled following removal of the hydroxymethylfurfural from the reaction mixture.

20. The process of claim 18 wherein the recycling comprises heating the reaction mixture following removal of the hydroxymethylfurfural therefrom for sufficient time to remove volatile substances therefrom.

21. A process for making a biofuel comprising:
   reacting a saccharide with a metal complex of an N-heterocyclic carbene so as to produce hydroxymethylfurfural, and
   using the hydroxymethylfurfural to prepare the biofuel;
wherein said saccharide is a hexose or a mixture of hexoses, or a dimer, oligomer or polymer or copolymer of a hexose or of a mixture thereof.

* * * * *